(12) United States Patent
Uretsky et al.

(10) Patent No.: US 9,131,686 B2
(45) Date of Patent: Sep. 15, 2015

(54) MICROBICIDAL COMPOSITIONS AND METHODS OF PRODUCTION USE THEREOF

(75) Inventors: Laura S. Uretsky, Milford, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/119,649

(22) PCT Filed: May 24, 2012

(86) PCT No.: PCT/US2012/039284
§ 371 (c)(1),
(2), (4) Date: Nov. 22, 2013

(87) PCT Pub. No.: WO2012/162466
PCT Pub. Date: Nov. 29, 2012

(65) Prior Publication Data
US 2014/0094424 A1    Apr. 3, 2014

Related U.S. Application Data

(60) Provisional application No. 61/489,874, filed on May 25, 2011.

(51) Int. Cl.
*A61K 31/70* (2006.01)
*A01N 43/16* (2006.01)
*A61K 31/19* (2006.01)
*A61K 31/7036* (2006.01)

(52) U.S. Cl.
CPC .............. *A01N 43/16* (2013.01); *A61K 31/19* (2013.01); *A61K 31/7036* (2013.01)

(58) Field of Classification Search
CPC .... A01N 43/16; A61K 31/16; A61K 31/7036
See application file for complete search history.

(56) References Cited

U.S. PATENT DOCUMENTS

| | | | |
|---|---|---|---|
| 3,091,572 A | 5/1963 | Luedemann et al. | |
| 5,464,850 A | 11/1995 | Voo et al. | |
| 7,135,197 B2 * | 11/2006 | Pena et al. | 424/653 |
| 7,183,100 B2 | 2/2007 | Candas et al. | |
| 2004/0248276 A1 | 12/2004 | Candas et al. | |
| 2005/0008671 A1 | 1/2005 | Van Antwerp | |
| 2005/0013836 A1 | 1/2005 | Raad | |
| 2006/0246208 A1 | 11/2006 | Mansouri et al. | |
| 2007/0093894 A1 | 4/2007 | Darouiche | |
| 2010/0285084 A1 | 11/2010 | Yang et al. | |

FOREIGN PATENT DOCUMENTS

WO    9513535 A1    5/1995

OTHER PUBLICATIONS

International Search Report of International Application No. PCT/US2012/039284 dated Nov. 5, 2012.
Written Opinion of International Application No. PCT/US2012/039284 dated Nov. 5, 2012.
Chinese Office Action of Chinese Patent Application No. 201280024689.0 dated Jul. 18, 2014.
European Search Report and Written Opinion of European Application No. 12790278.1 dated Nov. 11, 2014.
Cho et al., "Prophylactic Efficacy of a New Gentamicin-Releasing Urethral Catheter in Short-Term Catheterized Rabbits", Jan. 2001, BJU International, vol. 87 No. 1, pp. 104-109.

* cited by examiner

*Primary Examiner* — Elli Peselev
(74) *Attorney, Agent, or Firm* — Noam R. Pollack

(57) ABSTRACT

Microbicidal compositions that exhibit enhanced microbial efficacy are disclosed, as well as methods of producing and using the microbicidal compositions.

8 Claims, 1 Drawing Sheet

MICROBICIDAL COMPOSITIONS AND METHODS OF PRODUCTION USE THEREOF

CROSS REFERENCE TO RELATED APPLICATIONS

Not applicable.

STATEMENT REGARDING FEDERALLY SPONSORED RESEARCH OR DEVELOPMENT

Not Applicable.

FIELD OF THE INVENTION

The present application for patent relates to microbicidal compositions, as well as methods of producing and using same.

BACKGROUND

Clinical laboratory instruments are utilized for analysis of body fluids, such as but not limited to, whole blood, serum or plasma, in order to diagnose various conditions. In order to utilize these instruments, a broad range of reagents are necessary. Because these reagents contain nutrients for microorganisms, microbial growth is frequently a problem, especially for commercially distributed products, which often require months or years of shelf life in order to be commercially practical products.

One subcategory of such instruments and chemicals are those which are used in the critical care area, where the analytical results must be obtained quickly. These are used to measure items such as but not limited to, the concentrations in the blood of such components as carbon dioxide, oxygen, total hemoglobin, sodium, potassium, chloride, calcium, magnesium, lactate or glucose, as well as physical properties such as pH. In this environment, it is especially important that the systems work properly, because of the need for personnel to quickly make decisions regarding diagnosis and treatment of the patient. Therefore, microbicidal compositions are typically included in reagents utilized with critical care instruments to both keep the reagents uncontaminated during manufacturing and particularly to keep the instrument and sensors free of contamination during their use. Microbial contamination of an instrument will cause erroneous results, while microbial contamination of the reagent will cause the reagent to be unstable and potentially compromise the instrument.

There are presently various microbicidal compositions commercially available that are compatible with most prior art reagents and instruments. One example of a microbicidal composition utilized in such reagents is disclosed in U.S. Pat. No. 5,464,850, issued to Voo et al., on Nov. 7, 1995. However, these current microbicidal compositions are incompatible with enzyme based sensors; thus, the development of enzyme based sensors for use in these instruments requires that new and improved microbicidal compositions that are efficacious and do not adversely affect said enzymes be identified.

Thus, a need exists for new and improved microbicidal compositions that overcome the disadvantages and defects of the prior art compositions. It is to such compositions, and methods of producing and using same, that the presently disclosed and claimed inventive concept(s) is directed.

BRIEF DESCRIPTIONS OF THE DRAWINGS

Figure 1:
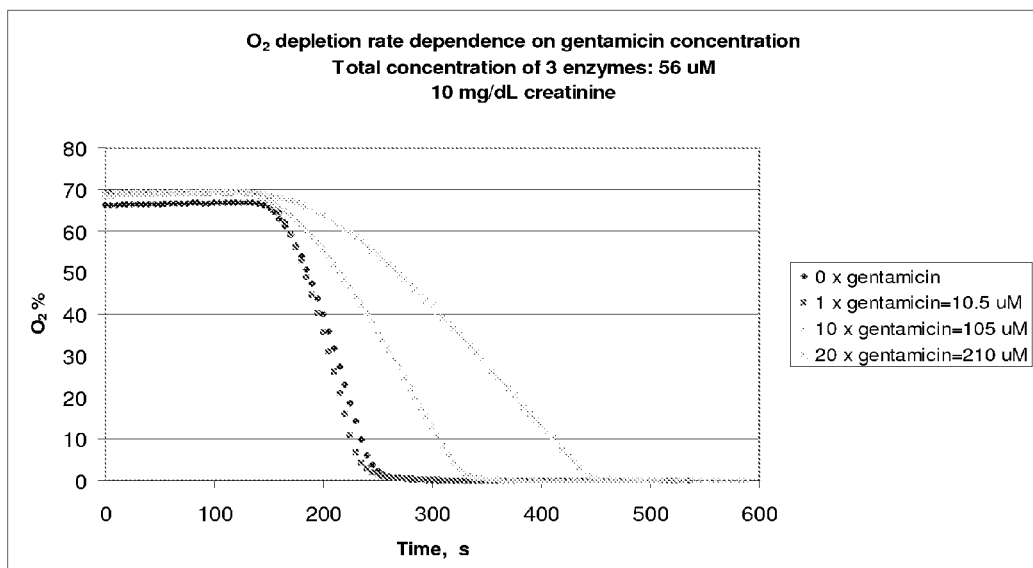

FIG. 1 graphically depicts the effects of exposure of a creatinine biosensor to various concentrations of gentamicin.

Figure 2:
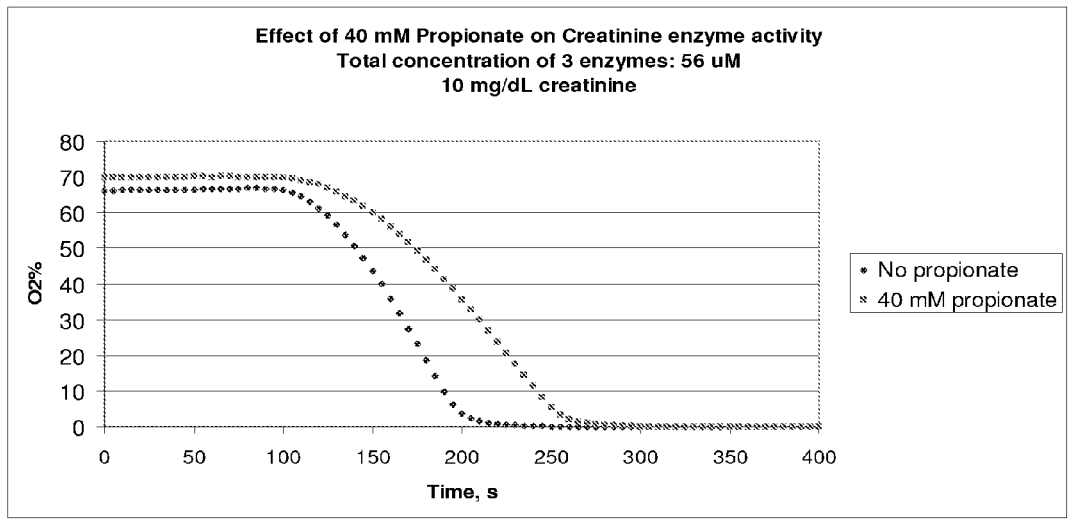

FIG. 2 graphically depicts the effects of exposure of a creatinine biosensor to various concentrations of propionate.

DETAILED DESCRIPTION OF EXEMPLARY EMBODIMENTS

The following detailed description and appendices describe and illustrate various exemplary embodiments. The description and drawings serve to enable one skilled in the art to make and use the invention, and are not intended to limit the scope of the invention in any manner.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which the presently disclosed and claimed inventive concept(s) pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of the presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "microbicidal composition" refers to a preservative composition that can substantially inhibit the growth of and/or kill microbes. For the purposes of this description, "microbes" may include bacteria, mold, yeast and/or viruses. Particular examples of microbes may include, but are not limited to, *Pseudomonas fluorescens*, *Pseudomonas putida*, *Pseudomonas aeruginosa*, *Ralstonia pickettii*, Gram positive rods, *Aspergillus glaucus*, and *Penicillium notatum*.

Gentamicin is an aminoglycoside antibiotic that is known to be effective against Gram-positive and Gram-negative bacteria. Gentamicin is known to be particularly effective against *Pseudomonas* species.

Propionates refer to salts of propionic acid. They are used as preservatives in food products (such as but not limited to, bread, chocolate products, cheese, etc.) as they are known to be nontoxic and to exhibit antifungal properties.

The term "biosensor" refers to a device for the detection of an analyte that combines a biological component with a physicochemical detector component. The biosensor comprises a biological component, such as but not limited to, enzymes, antibodies, tissue, microorganisms, organelles, cell receptors, nucleic acids, etc. For example but not by way of limitation, the biosensors utilized in accordance with the presently disclosed and claimed inventive concept(s) may be creatinine, blood urea nitrogen (BUN), glucose, lactate, etc.

As used herein, the phrase "does not substantially affect the biological activity of a sensor" means that a substantial amount of the sensor's biological (enzymatic) activity and stability is retained. For example but not by way of limitation, at least 30% of the biological activity of the sensor is retained, at least 40% of the biological activity of the sensor is retained, at least 50% of the biological activity of the sensor is retained, at least 60% of the biological activity is retained, at least 70% of the biological activity is retained, at least 80% of the biological activity is retained or at least 90% of the biological activity is retained. In addition, enzyme stability of the biosensor is substantially retained, whereby the enzyme stability of the biosensor extends for (for example but not by way of limitation) more than 4 days, more than 6 days, more than 8 days, more than 10 days, more than 12 days, more than 14 days, more than 20 days, more than 25 days, or more than 28 days.

The presently disclosed and claimed inventive concept(s) is directed to a microbicidal composition that is efficacious against various microorganisms (including, but not limited to, bacteria and mold) for an extended period of time (i.e., to the end of life of the product/reagent to which said composition is added). In addition, said microbicidal composition is compatible with the reagent into which it is disposed as well as any sensors present therein (including biosensors such as but not limited to, enzyme-based sensors), and is also compatible with any instruments with which it comes into contact including biosensors of the instrument; thus, the microbicidal composition does not adversely affect said instruments and does not adversely affect a biological activity and/or stability of said sensors. Therefore, the microbicidal composition provides a viable preservative for sensor-containing reagents and instruments as described herein.

The microbicidal composition includes gentamicin and at least one propionate, wherein a microbicidal synergy is observed between gentamicin and the propionate. As demonstrated herein below, the synergistic relationship maintains or enhances the effectiveness of either compound by itself, particularly for mold inhibition.

In one embodiment, the propionate present in the microbicidal composition is selected from the group consisting of calcium propionate, sodium propionate and combinations thereof.

The presently disclosed and claimed inventive concept(s) is also directed to a reagent solution that comprises the microbicidal composition described herein above. The reagent solution may be, for example, but not by way of limitation, a clinical chemistry reagent, and said clinical chemistry reagent may have a pH in a range of from about 6.0 to about 8.0.

The gentamicin and the at least one propionate may be present in the microbicidal composition and/or reagent solution at any concentration that allows the microbicidal composition to be efficacious against microorganisms while not substantially affecting the biological activity of at least one sensor present in the reagent solution, and thus any concentration that allows the microbicidal composition to function in accordance with the presently disclosed and claimed inventive concept(s) falls within the scope of the presently disclosed and claimed inventive concept(s).

In certain embodiments, the at least one propionate present in the microbicidal composition is calcium propionate, the concentration of calcium propionate in the microbicidal composition and/or reagent solution may be in a range of from about 0.25 mmol/L to about 2.5 mmol/L. In other embodiments, the propionate is sodium propionate, and the concentration of sodium propionate in the microbicidal composition and/or reagent solution may be in a range of from about 4 mmol/L to about 40 mmol/L. In certain embodiments, the concentration of gentamicin in the microbicidal composition and/or reagent solution may be in a range of from about 0.1% to about 1%.

The reagent solution may further include at least one biosensor, wherein the microbicidal composition does not substantially affect a biological activity of the at least one biosensor. Any biosensors known in the art or otherwise contemplated may be utilized in accordance with the presently disclosed and claimed inventive concept(s). For example but not by way of limitation, the biosensor may comprise creatinine, blood urea nitrogen (BUN), glucose and/or lactate. These types of sensors may utilize several enzymes (such as but not limited to, urease, creatinine amidohydrolase, creatinine amidinohydrolase, sarcosine oxidase, etc.) that are known to be adversely affected by the microbicidal compositions prior art, thus demonstrating one of the advantages of the presently disclosed and claimed inventive concept(s).

One or more biosensors may be part of an instrument. The instrument may be configured to bring the reagent solution into contact with the at least one of the biosensors. Alternatively, the Instrument may be part of a system in which the biosensors are brought into contact with the reagent solution of the present invention. The system may comprise the instrument containing the at least one biosensor and the microbicidal solution described above for cleaning the instruments and or its biosensors. The microbicidal solution may be part of a reagent solution that performs other functions for the instrument or sensors as further described herein. A kit containing at least one biosensor and the microbicidal solution or a reagent solution described herein may also be part of the system.

The presently disclosed and claimed inventive concept(s) is further directed to a method for killing microorganisms in an aqueous/reagent solution. Said method includes introducing to the aqueous/reagent solution the microbicidal composition described herein above.

The presently disclosed and claimed inventive concept(s) is further directed to a method for inhibiting growth of microorganisms in an aqueous/reagent solution. Said method includes introducing to the aqueous/reagent solution the microbicidal composition described herein above.

The presently disclosed and claimed inventive concept(s) is also directed to a method for killing microorganisms on a solid surface that is brought into contact with an aqueous/reagent solution. Said method includes introducing to the aqueous/reagent solution the microbicidal composition described herein above.

The presently disclosed and claimed inventive concept(s) is yet further directed to a method for inhibiting growth of microorganisms on a solid surface that is brought into contact with an aqueous/reagent solution. Said method includes introducing to the aqueous/reagent solution the microbicidal composition described herein above, and contacting a portion of the aqueous/reagent solution with the solid surface.

In certain embodiments, the microbicidal composition of the presently disclosed and claimed inventive concept(s) meets the following requirements: (1) soluble in aqueous solution at neutral pH and at an ionic strength in the range of 70 mM to 240 mM and preferably of 160 mM, and maintains pH within +/−0.005 over the life of the product; (2) effective against one or more of the following—gram negative bacteria, gram positive bacteria, molds and yeast; (3) stable so that at the end of life, the microbicidal composition retains microbial efficacy against the organisms of interest; (4) microbicide degradation products must not affect any of the analytical parameters (i.e., pH) or performance of the instrument; (5) compatible with all reagent components, including but not limited to, analytes, buffer, surfactant, etc.; (6) compatible with sensors, including but not limited to, biosensors (i.e., no interference, drift, or shortening of use life); (7) compatible with the instrument (i.e., no destruction, discoloration, etc. of parts); (8) compatible with all sample types used on the instrument (such as but not limited to, whole blood, serum, plasma, urine, control, etc.) without causing precipitation, color changes, or shifts in analytical values; (9) compatible with other microbicides contained in different reagents utilized on the same instrument; (10) non-hazardous to the user and easily disposed of at the concentration required in the reagents; (11) no toxicity hazard posed to production workers in the specific method for handling of the raw material during processing; and (12) material must meet US and WW regulatory requirements.

A summary of results shown in the Examples and obtained in the MBC (minimum bactericidal concentration) screen with various different compounds is shown in Table 1. These results demonstrate that the combination of gentamicin and propionate provided a greatly enhanced activity over either compound alone. Further, the combination was also much more efficacious against the tested bacteria and mold when compared to sulfamethoxazole, sodium azide, or a combination of sodium azide and propionates.

TABLE 1

| Summary of MBC Results | | | | | |
|---|---|---|---|---|---|
| Organism | Propionates | Na Azide | Azide/Propionates | Sulfamethoxazole | |
| P. fluorescens | No kill @ 100% @ 72 h | No kill @ 100% @ 72 h | No kill @ 100% @ 72 h | No kill @ 100% @ 72 h | |
| P. putida | No kill @ 100% @ 72 h | No kill @ 100% @ 72 h | No kill @ 100% @ 72 h | Total Kill @70% @ 48 h | Total Kill @ 20% @ 72 h |

TABLE 1-continued

Summary of MBC Results

| Organism | | | | |
|---|---|---|---|---|
| P. aeruginosa | No kill @ 100% @ 72 h | No kill @ 100% @ 72 h | No kill @ 100% @ 72 h | No kill @ 100% @ 72 h |
| Ralstonia pickettii | No kill @ 100% @ 72 h | No kill @ 100% @ 72 h | No kill @ 100% @ 72 h | No kill @ 100% @ 72 h |
| P. aeruginosa | No kill @ 100% @ 72 h | No kill @ 100% @ 72 h | No kill @ 100% @ 72 h | No kill @ 100% @ 72 h |
| Gram positive rods | No kill @ 100% @ 14 d | No kill @ 100% @ 14 d | No kill @ 100% @ 14 d | No kill @ 100% @ 14 d |
| Aspergillus glaucus | No kill @ 100% @ 14 d | No kill @ 100% @ 14 d | No kill @ 100% @ 14 d | No kill @ 100% @ 14 d |
| Penicillium notatum | No kill @ 100% @ 14 d | Total kill @ 50% @ 14 d | Total kill @ 30% @ 14 d | No kill @ 100% @ 14 d |

| Organism | Gentamicin | | Gentamicin/Propionates |
|---|---|---|---|
| P. fluorescens | Total kill @ 100% @ 24 h | Total kill @ 70% @ 48 h | Total kill @ 30% @ 72 h | Total kill @ 10% @ 8 h |
| P. putida | Total kill @ 10% @ 8 h | | | Total kill @ 10% @ 8 h |
| P. aeruginosa | Total kill @ 90% @ 48 h | Total kill @ 50% @ 72 h | | Total kill @ 70% @ 24 h |
| Ralstonia pickettii | Total kill @ 10% @ 8 h | | | Total kill @ 10% @ 48 h |
| P. aeruginosa | Total kill @ 30% @ 8 h | Total kill @ 10% @ 24 h | | Total kill @ 10% @ 8 h |
| Gram positive rods | Total kill @ 10% @ 8 h | | | Total kill @ 10% @ 8 h |
| Aspergillus glaucus | No Kill @ 100% @ 14 d | | | Total kill @ 100% @ 14 d |
| Penicillium notatum | No Kill @ 100% @ 14 d | | | Total kill @ 10% @ 14 d |

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

Minimum Bactericidal Concentration-1200XL Wash NEXT Reagent with Gentamicin and Sulfamethoxazole Wash NEXT base pool samples were prepared using 1% gentamicin, 1% sulfamethoxazole, 1% tetracycline and 1% novobiocin to be set up for minimum bactericidal testing. The tetracycline and novobiocin samples were not able to be used for this testing since neither antibiotic completely dissolved in the Wash reagent. The tetracycline sample resulted in a brownish-colored liquid which was also unable to be used due to its color. The gentamicin and sulfamethoxazole samples were tested against organisms isolated from manufacturing and field reagents.

The following is a summary of results obtained for Example 1, where either Gentamicin or sulfamethoxazole were added to the Wash NEXT Reagent.

When Gentamicin was added to the Wash NEXT reagent, the microbicidal activity against the following organisms was observed:

| | |
|---|---|
| P. fluorescens (D) | had total kill at 100% preservative at 24 hours |
| | had total kill at 70% preservative at 48 hours |
| | had total kill at 30% preservative at 72 hours |
| P. putida-DRO (K) | had total kill at 10% preservative at 8 hours |
| P. aeruginosa-KTO (L) | had total kill at 90% preservative at 48 hours |
| | had total kill at 50% preservative at 72 hours |
| Ralstonia pickettii (AU) | had total kill at 10% preservative at 8 hours |
| P. aeruginosa (AY) | had total kill at 30% preservative at 8 hours |
| | had total kill at 10% preservative at 24 hours |
| Gram positive rods (S) | had total kill at 10% preservative at 8 hours |

The molds were carried out to the 14-day time period, as they were still alive at the 72-hour time point.

| | |
|---|---|
| Aspergillus glaucus-DMO (Q) | never achieved total kill by the 14-day time point |
| Penicillium notatum-KMO (R) | never achieved total kill by the 14-day time point |

When Sulfamethoxazole was added to the Wash NEXT reagent, the microbicidal activity against the following organisms was observed:

| | |
|---|---|
| P. fluorescens (D) | never achieved total kill by the 72-hour time point |
| P. putida-DRO (K) | had total kill at 70% preservative at 48 hours |
| | had total kill at 20% preservative at 72 hours |
| P. aeruginosa-KTO (L) | never achieved total kill by the 72-hour time point |
| Ralstonia pickettii (AU) | never achieved total kill by the 72-hour time point |
| P. aeruginosa (AY) | never achieved total kill by the 72-hour time point |

The molds and gram positive rods were carried out to the 14-day time period, as they were still alive at the 72-hour time point.

| | |
|---|---|
| *Aspergillus glaucus*-DMO (Q) | never achieved total kill at the 14-day time point |
| *Penicillium notatum*-KMO (R) | never achieved total kill at the 14-day time point |
| Gram positive rods (S) | never achieved total kill at the 14-day time point |

Materials and Methods for Example 1:

The stock organisms were thawed and subbed prior to beginning the MBC test. Molds were subbed to SDA plates one week before, and the bacteria were subbed to TAT agar plates 24 hours prior to the start of the test. All plates were incubated at 32 degrees C.

Each bacterial organism was inoculated into 40 ml sterile saline in a centrifuge tube to create a density of MacFarland #1. Two serial dilutions of 1:100 were then made, resulting in $10^{-2}$ and $10^{-4}$ concentrations. Each dilution was vortexed before it was sampled, and sterile Eppendorf pipette tips were used to make each transfer. The $10^{-4}$ dilution was spiral plated to yield the initial inoculum concentration.

For the molds, each organism was inoculated into 40 ml sterile saline in a centrifuge tube to create a density of MacFarland #5. Two serial dilutions of 1:100 were then made, resulting in $10^{-2}$ and $10^{-4}$ concentrations. Each dilution was vortexed before it was sampled, and sterile Eppendorf pipette tips were used to make each transfer. The $10^{-4}$ dilution was spiral plated to yield the initial inoculum concentration.

MBC trays were set up with the prepared test reagent. Using a Matrix pipettor, 100 µl aliquots of reagent were distributed into the wells, diluting the amount of preservative from 100% to 10% increments, using unpreserved reagent as the diluent. In one row, 100% non-preserved reagent acted as a positive control and served as a benchmark for a full mat of growth. In well #12H, 100 µl unpreserved reagent was pipetted, and this well was not inoculated with organisms, as it served as the negative control. Once all of the trays were prepared, the prepared bacteria/mold suspensions were poured into the MBC inoculating trays. These were placed onto the reagent trays, and 0.01 ml inoculum was introduced into the 100 µl of reagent in each well.

At time points of 8 hours, 24 hours, 48 hours and 72 hours for bacteria, and additionally 7-day and 14-day for molds (and Gram+rods for the sulfamethoxazole), a test for growth was performed. This was done by dipping a sterile cotton swab into each well, and absorbing all of the liquid in the well. The swab was rolled onto a TAT agar plate ensuring that the entire swab touches the agar. Plates ware incubated at 32 degrees C. for 48 hours to 7 days, depending on the organism. Observations for growth were performed by a scoring matrix using + for a full mat, +/− for some growth, a numerical value for an actual colony count, and − for no growth.

Below are tables that contain the data obtained in Example 1. The MBC test is scored by (+) indicating a full grown mat of organisms, equivalent to the organisms in the unpreserved reagent. (+/−) indicates there is some kill evident disturbing that mat or bringing the quantities down to an almost countable level. An actual number is the actual number of colonies growing at that concentration of preservative. (−) indicates no growth found. The MBC trays were stored at room temperature for the entire test.

Tables 2-9 illustrate the results obtained with Gentamicin.

TABLE 2

*Pseudomonas fluorescens* (D)

| | 8 hour | 24 hour | 48 hour | 72 hour |
|---|---|---|---|---|
| 100% | +/− | − | − | − |
| 90% | +/− | 1 | − | − |
| 80% | +/− | 5 | − | − |
| 70% | +/− | 5 | − | − |
| 60% | +/− | 13 | +/− | − |
| 50% | +/− | 14 | +/− | − |
| 40% | + | +/− | +/− | − |
| 30% | + | +/− | +/− | − |
| 20% | + | + | +/− | 12 |
| 10% | + | + | +/− | 15 |
| 0% | + | + | + | + |

TABLE 3

*Pseudomonas putida* (K)

| | 8 hour | 24 hour | 48 hour | 72 hour |
|---|---|---|---|---|
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 4

*Pseudomonas aeruginosa* (L)

| | 8 hour | 24 hour | 48 hour | 72 hour |
|---|---|---|---|---|
| 100% | +/− | +/− | − | − |
| 90% | +/− | +/− | − | − |
| 80% | +/− | +/− | +/− | − |
| 70% | +/− | +/− | +/− | − |
| 60% | +/− | +/− | +/− | − |
| 50% | + | +/− | +/− | − |
| 40% | + | +/− | +/− | 1 |
| 30% | + | +/− | +/− | 2 |
| 20% | + | + | +/− | 4 |
| 10% | + | + | +/− | 8 |
| 0% | + | + | + | + |

TABLE 5

*Ralstonia pickettii* (AU)

| | 8 hour | 24 hour | 48 hour | 72 hour |
|---|---|---|---|---|
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 6

| | *Pseudomonas aeruginosa* (AY) | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | +/− | − | − | − |
| 10% | +/− | − | − | − |
| 0% | + | + | + | + |

TABLE 7

| | Gram + rods (S) | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 8

| *A. glaucus* (Q) | 8 hour | 24 hour | 48 hour | 72 hour | 7 day | 14 day |
|---|---|---|---|---|---|---|
| 100% | + | + | +/− | 18 | 5 | 4 |
| 90% | + | + | +/− | 22 | 10 | 9 |
| 80% | + | + | +/− | +/− | 16 | 14 |
| 70% | + | + | +/− | +/− | 21 | 20 |
| 60% | + | + | +/− | +/− | 25 | 26 |
| 50% | + | + | +/− | +/− | 29 | 28 |
| 40% | + | + | +/− | +/− | +/− | 35 |
| 30% | + | + | +/− | +/− | +/− | 36 |
| 20% | + | + | +/− | +/− | +/− | +/− |
| 10% | + | + | +/− | +/− | +/− | +/− |
| 0% | + | + | + | + | + | + |

TABLE 9

| *P. notatum* (R) | 8 hour | 24 hour | 48 hour | 72 hour | 7 day | 14 day |
|---|---|---|---|---|---|---|
| 100% | + | + | +/− | +/− | 7 | 6 |
| 90% | + | + | +/− | +/− | 11 | 9 |
| 80% | + | + | +/− | +/− | 16 | 12 |
| 70% | + | + | +/− | +/− | 23 | 18 |
| 60% | + | + | +/− | +/− | +/− | 23 |
| 50% | + | + | +/− | +/− | +/− | 25 |
| 40% | + | + | +/− | +/− | +/− | 28 |
| 30% | + | + | +/− | +/− | +/− | +/− |
| 20% | + | + | +/− | +/− | +/− | +/− |
| 10% | + | + | +/− | +/− | +/− | +/− |
| 0% | + | + | + | + | + | + |

TABLE 10

| | *Pseudomonas fluorescens* (D) | | | |
|---|---|---|---|---|
| | 8 hour | 24 hour | 48 hour | 72 hour |
| 100% | + | + | + | +/− |
| 90% | + | + | + | +/− |
| 80% | + | + | + | +/− |
| 70% | + | + | + | +/− |
| 60% | + | + | + | +/− |
| 50% | + | + | + | +/− |
| 40% | + | + | + | +/− |
| 30% | + | + | + | +/− |
| 20% | + | + | +/− | +/− |
| 10% | + | + | +/− | +/− |
| 0% | + | + | + | + |

TABLE 11

| | *Pseudomonas putida* (K) | | | |
|---|---|---|---|---|
| | 8 hour | 24 hour | 48 hour | 72 hour |
| 100% | + | + | − | − |
| 90% | + | + | − | − |
| 80% | + | + | − | − |
| 70% | + | + | − | − |
| 60% | + | +/− | 18 | − |
| 50% | + | +/− | 16 | − |
| 40% | + | +/− | 20 | − |
| 30% | + | +/− | 22 | − |
| 20% | + | +/− | +/− | − |
| 10% | + | 2 | +/− | +/− |
| 0% | + | + | + | + |

TABLE 12

| | *Pseudomonas aeruginosa* (L) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 13

| | *Ralstonia pickettii* (AU) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

Tables 10-17 illustrate the results obtained with Sulfamethoxazole.

TABLE 14

| | Pseudomonas aeruginosa (AY) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 15

| Gram + Rods (S) | 8 hour | 24 hour | 48 hour | 72 hour | 7 day | 14 day |
|---|---|---|---|---|---|---|
| 100% | + | + | + | + | + | + |
| 90% | + | + | + | + | + | + |
| 80% | + | + | + | + | + | + |
| 70% | + | + | + | + | + | + |
| 60% | + | + | + | + | + | + |
| 50% | + | + | + | + | + | + |
| 40% | + | + | + | + | + | + |
| 30% | + | + | + | + | + | + |
| 20% | + | + | + | + | + | + |
| 10% | + | + | + | + | + | + |
| 0% | + | + | + | + | + | + |

TABLE 16

| A. glaucus (Q) | 8 hour | 24 hour | 48 hour | 72 hour | 7 day | 14 day |
|---|---|---|---|---|---|---|
| 100% | + | + | +/− | 12 | 3 | 2 |
| 90% | + | + | +/− | 16 | 6 | 5 |
| 80% | + | + | +/− | 20 | 7 | 6 |
| 70% | + | + | +/− | 23 | 8 | 9 |
| 60% | + | + | +/− | +/− | 12 | 10 |
| 50% | + | + | +/− | +/− | 14 | 11 |
| 40% | + | + | +/− | +/− | 16 | 12 |
| 30% | + | + | +/− | +/− | +/− | +/− |
| 20% | + | + | +/− | +/− | +/− | +/− |
| 10% | + | + | +/− | +/− | +/− | +/− |
| 0% | + | + | + | + | + | + |

TABLE 17

| P. notatum (R) | 8 hour | 24 hour | 48 hour | 72 hour | 7 day | 14 day |
|---|---|---|---|---|---|---|
| 100% | + | + | +/− | 7 | 4 | 2 |
| 90% | + | + | +/− | 10 | 7 | 3 |
| 80% | + | + | +/− | 14 | 8 | 6 |
| 70% | + | + | +/− | 18 | 9 | 10 |
| 60% | + | + | +/− | +/− | +/− | 14 |
| 50% | + | + | +/− | +/− | +/− | 18 |
| 40% | + | + | +/− | +/− | +/− | 25 |
| 30% | + | + | +/− | +/− | +/− | 28 |
| 20% | + | + | +/− | +/− | +/− | 31 |
| 10% | + | + | +/− | + | + | +/− |
| 0% | + | + | + | + | + | + |

Table 18 lists the results of the negative MBC Controls as well as the initial concentrations utilized for each species in Example 1.

TABLE 18

| Organism | Negative MBC Control | Initial Concentration |
|---|---|---|
| P. fluorescens (D) | − | $4.0 \times 10^6$ |
| P. putida (K) | − | $4.2 \times 10^6$ |
| P. aeruginosa (L) | − | $4.6 \times 10^6$ |
| R. pickettii (AU) | − | $5.0 \times 10^6$ |
| P. aeruginosa (AY) | − | $4.3 \times 10^6$ |
| Gram + rods (S) | − | $1.6 \times 10^6$ |
| A. glaucus (Q) | − | $1.1 \times 10^5$ |
| P. notatum (R) | − | $1.1 \times 10^5$ |

Example 2

Minimum Bactericidal Concentration-1200XL Wash NEXT Reagent with (1) Sodium Azide, (2) Sodium and Calcium Propionates, (3) Sodium and Calcium Propionates Plus Sodium Azide, and (4) Sodium and Calcium Propionates Plus Gentamicin Wash NEXT base pool samples were prepared using 0.09% sodium azide and also sodium and calcium propionates as preservatives. Wash samples with the two propionates were also tested with sodium azide added to one and gentamicin added to the other. All four samples were set up for minimum bactericidal testing and were tested against organisms isolated from manufacturing and field reagents.

The following is a summary of results obtained for Example 2, where sodium azide, propionates and/or gentamicin were added to the Wash NEXT Reagent. In all instances, the molds were carried out to the 14-day time period, as they were still alive at the 72-hour time point. In all instances except when propionates and gentamicin were added to the Wash NEXT reagent, the gram positive rods were also carried out to the 14-day time period, as they were still alive at the 72-hour time point.

The materials and methods and analysis of the MBC test were the same as in Example 1.

When Sodium Azide was added to the Wash NEXT reagent, the microbicidal activity against the following organisms was observed:

| | |
|---|---|
| P. fluorescens (D) | never achieved total kill by the 72 hour time point |
| P. putida-DRO (K) | never achieved total kill by the 72 hour time point |
| P. aeruginosa-KTO (L) | never achieved total kill by the 72 hour time point |
| Ralstonia pickettii (AU) | never achieved total kill by the 72 hour time point |
| P. aeruginosa (AY) | never achieved total kill by the 72 hour time point |
| Gram positive rods (S) | never achieved total kill by the 14-day time point |
| Aspergillus glaucus-DMO (Q) | never achieved total kill by the 14-day time point |
| Penicillium notatum-KMO (R) | had total kill at 50% preservative at 14 days |

When Sodium and Calcium Propionates were added to the Wash NEXT reagent, the microbicidal activity against the following organisms was observed:

| | |
|---|---|
| P. fluorescens (D) | never achieved total kill by the 72-hour time point |
| P. putida-DRO (K) | never achieved total kill by the 72 hour time point |

-continued

| | |
|---|---|
| *P. aeruginosa*-KTO (L) | never achieved total kill by the 72-hour time point |
| *Ralstonia pickettii* (AU) | never achieved total kill by the 72-hour time point |
| *P. aeruginosa* (AY) | never achieved total kill by the 72-hour time point |
| *Aspergillus glaucus*-DMO (Q) | never achieved total kill at the 14-day time point |
| *Penicillium notatum*-KMO (R) | never achieved total kill at the 14-day time point |
| Gram positive rods (S) | never achieved total kill at the 14-day time point |

When Sodium and Calcium Propionates plus Sodium Azide were added to the Wash NEXT reagent, the microbicidal activity against the following organisms was observed:

| | |
|---|---|
| *P. fluorescens* (D) | never achieved total kill by the 72-hour time point |
| *P. putida*-DRO (K) | never achieved total kill by the 72 hour time point |
| *P. aeruginosa*-KTO (L) | never achieved total kill by the 72-hour time point |
| *Ralstonia pickettii* (AU) | never achieved total kill by the 72-hour time point |
| *P. aeruginosa* (AY) | never achieved total kill by the 72-hour time point |
| *Aspergillus glaucus*-DMO (Q) | never achieved total kill at the 14-day time point |
| *Penicillium notatum*-KMO (R) | had total kill at 30% preservative at 14 days |
| Gram positive rods (S) | never achieved total kill at the 14-day time point |

When Sodium and Calcium Propionates plus Gentamicin were added to the Wash NEXT reagent, the microbicidal activity against the following organisms was observed:

| | |
|---|---|
| *P. fluorescens* (D) | had total kill at 10% preservative at 8 hours |
| *P. putida*-DRO (K) | had total kill at 10% preservative at 8 hours |
| *P. aeruginosa*-KTO (L) | had total kill at 70% preservative at 24 hours |
| *Ralstonia pickettii* (AU) | had total kill at 10% preservative at 48 hours |
| *P. aeruginosa* (AY) | had total kill at 10% preservative at 8 hours |
| Gram positive rods (S) | had total kill at 10% preservative at 8 hours |
| *Aspergillus glaucus*-DMO (Q) | had total kill at 100% preservative at 14 days |
| *Penicillium notatum*-KMO (R) | had total kill at 10% preservative at 14 days |

Below are tables that contain the data obtained in Example 2.

Tables 19-26 illustrate the results obtained with Sodium Azide.

TABLE 19

| *Pseudomonas fluorescens* (D) | | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |

TABLE 19-continued

| *Pseudomonas fluorescens* (D) | | | | |
|---|---|---|---|---|
| | 8 hour | 24 hour | 48 hour | 72 hour |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 20

| *Pseudomonas putida* (K) | | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 21

| *Pseudomonas aeruginosa* (L) | | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 22

| *Ralstonia pickettii* (AU) | | | | |
|---|---|---|---|---|
| | 8 hour | 24 hour | 48 hour | 72 hour |
| 100% | + | +/− | +/− | 2 |
| 90% | + | +/− | +/− | 4 |
| 80% | + | +/− | +/− | 7 |
| 70% | + | + | +/− | 8 |
| 60% | + | + | +/− | 10 |
| 50% | + | + | +/− | +/− |
| 40% | + | + | +/− | +/− |
| 30% | + | + | +/− | +/− |
| 20% | + | + | + | +/− |
| 10% | + | + | + | + |
| 0% | + | + | + | + |

TABLE 23

| | *Pseudomonas aeruginosa* (AY) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 24

| Gram positive rods (S) | 8 hour | 24 hour | 48 hour | 72 hour | 7 day | 14 day |
|---|---|---|---|---|---|---|
| 100% | + | + | + | + | + | + |
| 90% | + | + | + | + | + | + |
| 80% | + | + | + | + | + | + |
| 70% | + | + | + | + | + | + |
| 60% | + | + | + | + | + | + |
| 50% | + | + | + | + | + | + |
| 40% | + | + | + | + | + | + |
| 30% | + | + | + | + | + | + |
| 20% | + | + | + | + | + | + |
| 10% | + | + | + | + | + | + |
| 0% | + | + | + | + | + | + |

TABLE 25

| *A. glaucus* (Q) | 8 hour | 24 hour | 48 hour | 72 hour | 7 day | 14 day |
|---|---|---|---|---|---|---|
| 100% | + | + | + | + | + | +/− |
| 90% | + | + | + | + | + | +/− |
| 80% | + | + | + | + | + | +/− |
| 70% | + | + | + | + | + | +/− |
| 60% | + | + | + | + | + | +/− |
| 50% | + | + | + | + | + | +/− |
| 40% | + | + | + | + | + | +/− |
| 30% | + | + | + | + | + | +/− |
| 20% | + | + | + | + | + | +/− |
| 10% | + | + | + | + | + | +/− |
| 0% | + | + | + | + | + | + |

TABLE 26

| *P. notatum* (R) | 8 hour | 24 hour | 48 hour | 72 hour | 7 day | 14 day |
|---|---|---|---|---|---|---|
| 100% | + | + | +/− | 6 | 3 | − |
| 90% | + | + | +/− | 7 | 4 | − |
| 80% | + | + | +/− | 9 | 6 | − |
| 70% | + | + | +/− | 11 | 9 | − |
| 60% | + | + | +/− | 13 | 10 | − |
| 50% | + | + | +/− | 15 | 12 | − |
| 40% | + | + | +/− | 18 | 15 | 6 |
| 30% | + | + | +/− | 22 | 19 | 8 |
| 20% | + | + | +/− | 22 | 19 | 11 |
| 10% | + | + | +/− | 24 | 20 | 14 |
| 0% | + | + | + | + | + | + |

TABLE 27

| | *Pseudomonas fluorescens* (D) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 28

| | *Pseudomonas putida* (K) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 29

| | *Pseudomonas aeruginosa* (L) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 30

| | *Ralstonia pickettii* (AU) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

Tables 27-34 illustrate the results obtained with Sodium and Calcium Propionates.

TABLE 31

| | *Pseudomonas aeruginosa* (AY) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 32

| Gram + Rods (S) | 8 hour | 24 hour | 48 hour | 72 hour | 7 day | 14 day |
|---|---|---|---|---|---|---|
| 100% | + | + | + | + | + | + |
| 90% | + | + | + | + | + | + |
| 80% | + | + | + | + | + | + |
| 70% | + | + | + | + | + | + |
| 60% | + | + | + | + | + | + |
| 50% | + | + | + | + | + | + |
| 40% | + | + | + | + | + | + |
| 30% | + | + | + | + | + | + |
| 20% | + | + | + | + | + | + |
| 10% | + | + | + | + | + | + |
| 0% | + | + | + | + | + | + |

TABLE 33

| *A. glaucus* (Q) | 8 hour | 24 hour | 48 hour | 72 hour | 7 day | 14 day |
|---|---|---|---|---|---|---|
| 100% | + | + | + | + | + | +/− |
| 90% | + | + | + | + | + | +/− |
| 80% | + | + | + | + | + | +/− |
| 70% | + | + | + | + | + | + |
| 60% | + | + | + | + | + | + |
| 50% | + | + | + | + | + | + |
| 40% | + | + | + | + | + | + |
| 30% | + | + | + | + | + | + |
| 20% | + | + | + | + | + | + |
| 10% | + | + | + | + | + | + |
| 0% | + | + | + | + | + | + |

TABLE 34

| *P. notatum* (R) | 8 hour | 24 hour | 48 hour | 72 hour | 7 day | 14 day |
|---|---|---|---|---|---|---|
| 100% | + | + | +/− | 2 | 3 | 3 |
| 90% | + | + | +/− | 5 | 5 | 6 |
| 80% | + | + | +/− | 9 | 8 | 7 |
| 70% | + | + | +/− | 12 | 11 | 10 |
| 60% | + | + | +/− | 16 | 13 | 11 |
| 50% | + | + | +/− | 20 | 15 | 14 |
| 40% | + | + | +/− | 22 | 17 | 16 |
| 30% | + | + | +/− | 24 | 19 | 20 |
| 20% | + | + | +/− | 27 | 23 | 23 |
| 10% | + | + | 6 | 30 | 25 | 24 |
| 0% | + | + | + | + | + | + |

TABLE 35

| | *Pseudomonas fluorescens* (D) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 36

| | *Pseudomonas putida* (K) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 37

| | *Pseudomonas aeruginosa* (L) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 38

| | *Ralstonia pickettii* (AU) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

Tables 35-42 illustrate the results obtained with Sodium and Calcium Propionates and Sodium Azide.

TABLE 39

| | Pseudomonas aeruginosa (AY) | | | |
|---|---|---|---|---|
| | 8 hour | 24 hour | 48 hour | 72 hour |
| 100% | + | + | + | + |
| 90% | + | + | + | + |
| 80% | + | + | + | + |
| 70% | + | + | + | + |
| 60% | + | + | + | + |
| 50% | + | + | + | + |
| 40% | + | + | + | + |
| 30% | + | + | + | + |
| 20% | + | + | + | + |
| 10% | + | + | + | + |
| 0% | + | + | + | + |

TABLE 40

| Gram + Rods (S) | 8 hour | 24 hour | 48 hour | 72 hour | 7 day | 14 day |
|---|---|---|---|---|---|---|
| 100% | + | + | + | + | + | + |
| 90% | + | + | + | + | + | + |
| 80% | + | + | + | + | + | + |
| 70% | + | + | + | + | + | + |
| 60% | + | + | + | + | + | + |
| 50% | + | + | + | + | + | + |
| 40% | + | + | + | + | + | + |
| 30% | + | + | + | + | + | + |
| 20% | + | + | + | + | + | + |
| 10% | + | + | + | + | + | + |
| 0% | + | + | + | + | + | + |

TABLE 41

| A. glaucus (Q) | 8 hour | 24 hour | 48 hour | 72 hour | 7 day | 14 day |
|---|---|---|---|---|---|---|
| 100% | + | + | +/− | +/− | +/− | 10 |
| 90% | + | + | +/− | +/− | +/− | 12 |
| 80% | + | + | +/− | +/− | +/− | 16 |
| 70% | + | + | +/− | +/− | +/− | 20 |
| 60% | + | + | +/− | +/− | +/− | 22 |
| 50% | + | + | +/− | +/− | +/− | +/− |
| 40% | + | + | + | + | +/− | +/− |
| 30% | + | + | + | + | + | +/− |
| 20% | + | + | + | + | + | +/− |
| 10% | + | + | + | + | + | +/− |
| 0% | + | + | + | + | + | + |

TABLE 42

| P. notatum (R) | 8 hour | 24 hour | 48 hour | 72 hour | 7 day | 14 day |
|---|---|---|---|---|---|---|
| 100% | + | + | +/− | +/− | 2 | − |
| 90% | + | + | +/− | +/− | 5 | − |
| 80% | + | + | +/− | +/− | 6 | − |
| 70% | + | + | +/− | +/− | 8 | − |
| 60% | + | + | +/− | +/− | 10 | − |
| 50% | + | + | +/− | +/− | 12 | − |
| 40% | + | + | +/− | +/− | 14 | − |
| 30% | + | + | +/− | +/− | 18 | − |
| 20% | + | + | +/− | +/− | 21 | 20 |
| 10% | + | + | +/− | +/− | + | 25 |
| 0% | + | + | + | + | + | + |

TABLE 43

| | Pseudomonas fluorescens (D) | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 44

| | Pseudomonas putida (K) | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 45

| | Pseudomonas aeruginosa (L) | | | |
|---|---|---|---|---|
| | 8 hour | 24 hour | 48 hour | 72 hour |
| 100% | +/− | − | − | − |
| 90% | +/− | − | − | − |
| 80% | +/− | − | − | − |
| 70% | +/− | − | − | − |
| 60% | +/− | +/− | − | − |
| 50% | +/− | +/− | +/− | 7 |
| 40% | +/− | +/− | +/− | 13 |
| 30% | +/− | +/− | +/− | +/− |
| 20% | + | +/− | +/− | +/− |
| 10% | + | +/− | +/− | +/− |
| 0% | + | + | + | + |

TABLE 46

| | Ralstonia pickettii (AU) | | | |
|---|---|---|---|---|
| | 8 hour | 24 hour | 48 hour | 72 hour |
| 100% | + | +/− | − | − |
| 90% | + | +/− | − | − |
| 80% | + | +/− | − | − |
| 70% | + | +/− | − | − |
| 60% | + | +/− | − | − |
| 50% | + | +/− | − | − |
| 40% | + | +/− | − | − |
| 30% | + | +/− | − | − |
| 20% | + | +/− | − | − |
| 10% | + | +/− | − | − |
| 0% | + | + | + | + |

Tables 43-50 illustrate the results obtained with Sodium and Calcium Propionates and Gentamicin.

TABLE 47

| Pseudomonas aeruginosa (AY) | | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 48

| Gram + Rods (S) | | | | |
|---|---|---|---|---|
| | 8 hour | 24 hour | 48 hour | 72 hour |
| 100% | − | − | − | − |
| 90% | − | − | − | − |
| 80% | − | − | − | − |
| 70% | − | − | − | − |
| 60% | − | − | − | − |
| 50% | − | − | − | − |
| 40% | − | − | − | − |
| 30% | − | − | − | − |
| 20% | − | − | − | − |
| 10% | − | − | − | − |
| 0% | + | + | + | + |

TABLE 49

| A. glaucus (Q) | 8 hour | 24 hour | 48 hour | 72 hour | 7 day | 14 day |
|---|---|---|---|---|---|---|
| 100% | + | + | +/− | +/− | +/− | − |
| 90% | + | + | +/− | +/− | +/− | 3 |
| 80% | + | + | +/− | +/− | +/− | 5 |
| 70% | + | + | +/− | +/− | +/− | 8 |
| 60% | + | + | +/− | +/− | +/− | 9 |
| 50% | + | + | +/− | +/− | +/− | 13 |
| 40% | + | + | + | + | + | +/− |
| 30% | + | + | + | + | + | +/− |
| 20% | + | + | + | + | + | +/− |
| 10% | + | + | + | + | + | +/− |
| 0% | + | + | + | + | + | + |

TABLE 50

| P. notatum (R) | 8 hour | 24 hour | 48 hour | 72 hour | 7 day | 14 day |
|---|---|---|---|---|---|---|
| 100% | + | + | +/− | +/− | 4 | − |
| 90% | + | + | +/− | +/− | 8 | − |
| 80% | + | + | +/− | +/− | 12 | − |
| 70% | + | + | +/− | +/− | 15 | − |
| 60% | + | + | +/− | +/− | +/− | − |
| 50% | + | + | +/− | +/− | +/− | − |
| 40% | + | + | +/− | +/− | +/− | − |
| 30% | + | + | +/− | +/− | +/− | − |
| 20% | + | + | +/− | +/− | +/− | − |
| 10% | + | + | +/− | +/− | + | − |
| 0% | + | + | + | + | + | + |

Table 51 lists the results of the negative MBC Controls as well as the initial concentrations utilized for each species in Example 2.

TABLE 51

| Organism | Negative MBC Control | Initial Concentration |
|---|---|---|
| P. fluorescens (D) | − | $4.1 \times 10^6$ |
| P. putida (K) | − | $2.2 \times 10^6$ |
| P. aeruginosa (L) | − | $1.7 \times 10^6$ |
| R. pickettii (AU) | − | $4.6 \times 10^6$ |
| P. aeruginosa (AY) | − | $4.9 \times 10^6$ |
| Gram + rods (S) | − | $1.6 \times 10^6$ |
| A. glaucus (Q) | − | $1.4 \times 10^5$ |
| P. notatum (R) | − | $1.2 \times 10^5$ |

Based on this testing, the best combination of preservatives used with Wash NEXT was Na and Ca propionates in combination with gentamicin. All organisms tested were killed off by the 14-day test point.

Example 3

Analysis of the Effects of Gentamicin and Propionate on Enzymatic Activity of Biosensors In FIG. 1, the effects of various concentrations of gentamicin on the enzymatic activity of a creatinine biosensor (comprising the three enzymes creatinine amidohydrolase, creatinine amidinohydrolase and sarcosine oxidase) were determined. In FIG. 2, the effects of various concentrations of propionate on the enzymatic activity of a creatinine biosensor (comprising three enzymes) were determined.

In both instances, a decreasing rate of $O_2\%$ is an indicator of enzyme activity; the faster the rate of $O_2\%$ decrease, the higher enzymatic activity is.

In FIG. 1, a high concentration of gentamicin (210 μM) was utilized, and said concentration did not inactivate enzymatic activity of the three enzymes in the creatinine biosensor.

In FIG. 2, a concentration of 40 mM propionate did not substantially affect the enzymatic activity of the three enzymes in the creatinine biosensor.

Therefore, Example 3 demonstrates that the microbicidal compositions of the presently disclosed and claimed inventive concept(s) do not degrade enzymatic activity of a biosensor.

Thus, in accordance with the presently disclosed and claimed inventive concept(s), there have been provided microbicidal compositions with enhanced microbial efficacy, as well as methods of producing and using same, which fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

What is claimed is:

1. A system, comprising:
    a microbicidal composition for inhibiting growth of microbes comprising gentamicin and at least one propionate;
    at least one biosensor; and
    a means for applying said microbicidal composition to at least a portion of said biosensor and wherein the microbicidal composition does not substantially affect a biological activity of the at least one biosensor.

2. The system of claim 1, wherein the at least one propionate of the microbicidal composition is selected from the group consisting of calcium propionate, sodium propionate and combinations thereof.

3. The system of claim 2, wherein the propionate is calcium propionate, and the concentration of calcium propionate is in a range of from about 0.25 mmol/L to about 2.5 mmol/L.

4. The system of claim 2, wherein the propionate is sodium propionate, and the concentration of sodium propionate is in a range of from about 4 mmol/L to about 40 mmol/L.

5. The system of claim 1, wherein the concentration of gentamicin is in a range of from about 0.1% to about 1%.

6. The system of claim 1, wherein said microbicidal composition has a pH in a range of from about 6.0 to about 8.0.

7. The system of claim 1, wherein the at least one biosensor comprises creatinine.

8. The system of claim 1, wherein the at least one biosensor comprises blood urea nitrogen (BUN).

* * * * *